(12) United States Patent
Dehkordi et al.

(10) Patent No.: US 12,013,340 B2
(45) Date of Patent: Jun. 18, 2024

(54) APPARATUS AND METHOD FOR OPTICALLY CHARACTERIZING A TEXTILE SAMPLE

(71) Applicant: Uster Technologies AG, Uster (CH)

(72) Inventors: Peyman Dehkordi, Knoxville, TN (US); Kent A. Rinehart, Knoxville, TN (US); David Dickson McAlister, III, Knoxville, TN (US)

(73) Assignee: Uster Technologies AG, Uster (CH)

( * ) Notice: Subject to any disclaimer, the term of this patent is extended or adjusted under 35 U.S.C. 154(b) by 165 days.

(21) Appl. No.: 17/632,429

(22) PCT Filed: Nov. 6, 2019

(86) PCT No.: PCT/CH2019/000032
§ 371 (c)(1),
(2) Date: Feb. 2, 2022

(87) PCT Pub. No.: WO2021/087626
PCT Pub. Date: May 14, 2021

(65) Prior Publication Data
US 2022/0276168 A1 Sep. 1, 2022

(51) Int. Cl.
*G01N 21/64* (2006.01)
*G01N 21/17* (2006.01)
(Continued)

(52) U.S. Cl.
CPC ....... *G01N 21/6456* (2013.01); *G01N 21/256* (2013.01); *G01N 21/276* (2013.01);
(Continued)

(58) Field of Classification Search
CPC ............. G01N 21/6456; G01N 21/256; G01N 21/276; G01N 21/31; G01N 21/55;
(Continued)

(56) References Cited

U.S. PATENT DOCUMENTS 4,019,066 A * 4/1977 Lucas .................... G01B 11/30
356/600
5,998,351 A * 12/1999 Brouwer .................. C11D 3/42
510/351
(Continued)

FOREIGN PATENT DOCUMENTS

| EP | 0293810 B1 | 4/1991 | |
| WO | 2013017738 A1 | 2/2013 | |
| WO | WO2013017738 A1 * | 2/2013 | ............. B41M 3/14 |
| WO | 2019210436 A1 | 11/2019 | |

OTHER PUBLICATIONS

U.S. Appl. No. 62/666,125, filed May 3, 2018, Peyman Dehkordi.

*Primary Examiner* — David P Porta
*Assistant Examiner* — Gisselle M Gutierrez
(74) *Attorney, Agent, or Firm* — TechnicalAttorney; Rick Barnes

(57) ABSTRACT

An apparatus (100) for optically characterizing a textile sample (106) comprises a presentation subsystem (102) comprising a viewing window (108). A radiation subsystem (114) comprises a radiation source (120) for directing a first, ultraviolet radiation (122) and a second, visible radiation (123) toward the sample (106), and causing the sample (106) to produce a fluorescent radiation (124) and a reflected radiation (125). A sensing subsystem (126) comprises an imager (130) for capturing the fluorescent radiation (124) and the reflected radiation (125) in an array of pixels (408). A control subsystem (132) comprises a processor (136) for controlling the presentation subsystem (102), the radiation subsystem (114), and the sensing subsystem (126), and for creating a fluorescent and reflected radiation image (400) containing both spectral information and spatial information in regard to the fluorescent radiation (124) and the reflected radiation (125).

26 Claims, 10 Drawing Sheets

(51) Int. Cl.
*G01N 21/25* (2006.01)
*G01N 21/27* (2006.01)
*G01N 21/31* (2006.01)
*G01N 21/47* (2006.01)
*G01N 21/55* (2014.01)
*G01N 33/36* (2006.01)

(52) U.S. Cl.
CPC .............. *G01N 21/31* (2013.01); *G01N 21/55* (2013.01); *G01N 33/367* (2013.01); *G01N 2021/174* (2013.01); *G01N 2021/178* (2013.01); *G01N 2021/3155* (2013.01); *G01N 2021/4766* (2013.01); *G01N 2021/6423* (2013.01); *G01N 2021/6471* (2013.01)

(58) Field of Classification Search
CPC ........... G01N 33/367; G01N 2021/174; G01N 2021/178; G01N 2021/3155; G01N 2021/4766; G01N 2021/6423; G01N 2021/6471; G01N 33/36; G01N 2021/3174; G01N 2021/8444; G01N 2021/8645; G01N 2021/8845; G01N 21/8983; G01N 2021/1765
See application file for complete search history.

(56) References Cited

U.S. PATENT DOCUMENTS

| | | | |
|---|---|---|---|
| 2006/0132777 A1* | 6/2006 | Hubble, II | G01N 21/64 356/402 |
| 2008/0144013 A1* | 6/2008 | Lanoue | G01J 3/02 356/73 |
| 2013/0155402 A1 | 6/2013 | Walton et al. | |
| 2014/0008538 A1* | 1/2014 | Soltau | G01T 1/2928 378/161 |
| 2014/0285798 A1* | 9/2014 | Nishimura | G01J 3/26 356/300 |
| 2015/0131090 A1* | 5/2015 | Osumi | G01J 3/1256 356/300 |
| 2016/0258881 A1 | 9/2016 | Bown et al. | |
| 2018/0052116 A1* | 2/2018 | Dehkordi | G01N 21/8806 |
| 2019/0025208 A1* | 1/2019 | Horigome | G01J 3/0254 |
| 2019/0025209 A1* | 1/2019 | Horigome | G01N 21/31 |
| 2019/0195689 A1* | 6/2019 | McQuilkin | G01J 3/36 |
| 2021/0156802 A1* | 5/2021 | Dehkordi | G01N 21/93 |
| 2021/0315496 A1* | 10/2021 | Carvalho de Sousa | A61B 5/150358 |
| 2023/0159675 A1* | 5/2023 | Jimbo | C08F 20/38 526/257 |

* cited by examiner

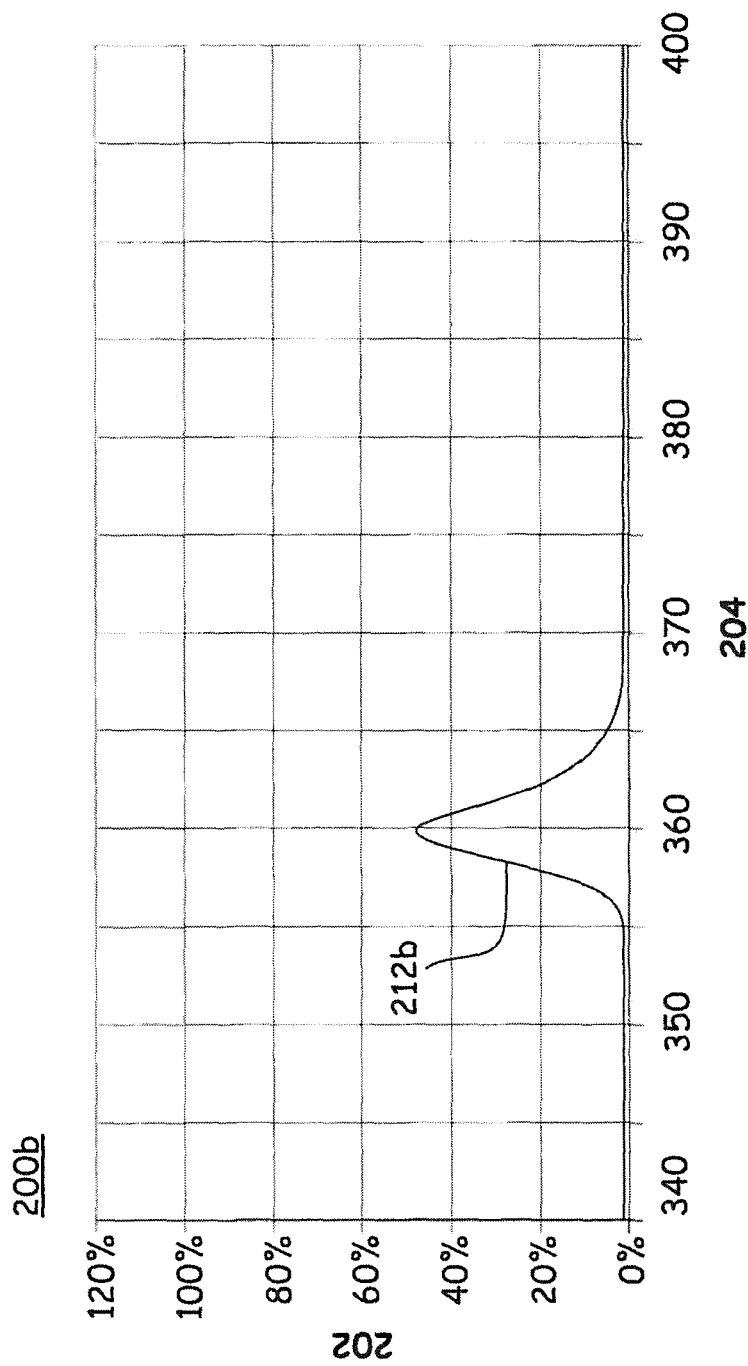

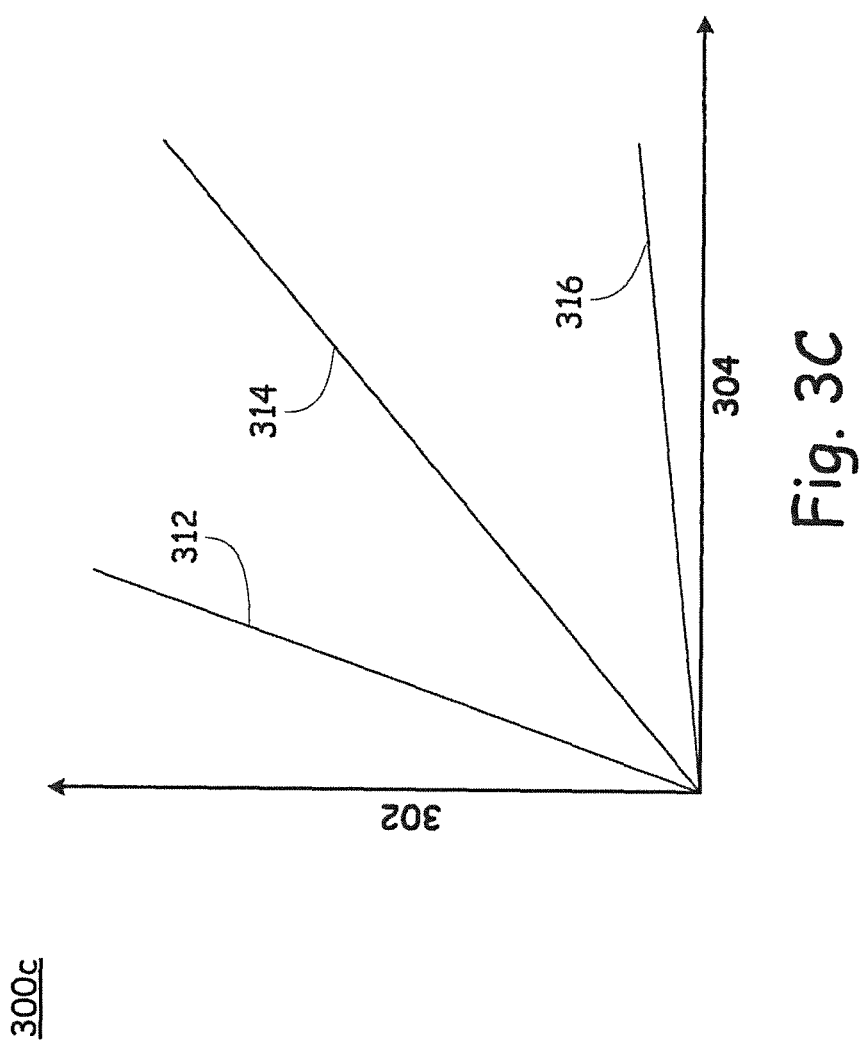

APPARATUS AND METHOD FOR OPTICALLY CHARACTERIZING A TEXTILE SAMPLE

FIELD

This invention relates to the field of textile characteristics measurement. More particularly, this invention relates to an apparatus and a method for optically characterizing a textile sample. The invention can be used in online and offline applications.

INTRODUCTION

Textiles are woven or knitted fabrics made from yarn, but they also include fibers (natural, manmade, and blend), yarn, or any other product made from these combinations. The visual perception of the final fabric is very important to the end user. Visual perception includes, but is not limited to, pattern, color, and brightness. Brightness is commonly defined as an attribute of visual perception in which a source appears to be radiating or reflecting light. For textile, the brightness is a function of reflected light and fluorescence emission. Fluorescent pigments are one method of adding brightness to the fabric. A fluorescent material is defined as a material that emits optical radiation after having absorbed light or other electromagnetic radiation, typically at wavelengths that are longer than the wavelengths of the electromagnetic radiation absorbed. Therefore, fluorescent material not only reflects the incident light but also emits an additional light at longer wavelengths. Especially if the absorbed electromagnetic radiation is in the ultraviolet (UV) range and the emitted light is visible, the fluorescent material appears to be brighter.

There are at least three major categories of fluorescent pigments: inorganic fluors, optical whiteners, and daylight fluorescents. Their major differences are in their chemical composition and optical characteristics, and thus their application. For example, inorganic fluors are usually activated by optical radiations in the range of ultraviolet (UV) to visible (300-420 nm) light, whereas optical whiteners are activated in the range of near UV (340-400 nm), and daylight fluorescents are activated and emit in the visible range (400-700 nm).

Fluorescent properties can be given to textiles in a variety of ways, such as, but not limited to (a) coating fabrics with fluorescent material in a resin mix, (b) introducing fluorescent material to the fibers at the spinning stage, (c) coating the fibers, and (d) textile finishing or domestic laundering with fluorescent material.

The quality and application of the fluorescent pigments are important parameters to maintain, monitor, and control for best cosmetic performance in the textile process. While these methods have been around for many years, the formulation and quality control of the fluorescent material application have been challenging, primarily due to lack of proper measurement instrumentation and lack of understanding of the fluorescent material.

US-2015/0131090 A1 discloses a multi-angle spectral imaging measurement method and apparatus. A lighting device that emits illumination light from two or more angular directions onto a sample surface to be measured, an imaging optical lens, and a monochrome two-dimensional image sensor are provided. This configuration provides a method and an apparatus that take a two-dimensional image of the sample surface to be measured at each measurement wavelength and accurately measures multi-angle and spectral information on each of all pixels in the two-dimensional image in a short time. In one embodiment, a fluorescent object is illuminated with monochromatic light and a spectral light receiver is used so that fluorescent color can be measured.

US-2016/0258881 A1 discloses a method of marking an industrial process material including selectively incorporating a luminescent marker onto and/or into the industrial process material in a trace amount insufficient to be optically detectable in the presence of ambient light but sufficient to be non-destructively optically detectable in and/or on the industrial process material in situ in the field or on-site. The material is illuminated with light of a certain wavelength. When the luminescent marker is present in the material, it emits luminescent light of a characteristic wavelength. Light emitted by the material is detected by a spectrometer that can include a CCD chip as the light-sensitive element.

SUMMARY

It is an object of the present invention to characterize even more completely a textile sample with regard to its optical properties.

This and other objects are achieved by the apparatus and the method defined in the independent claims. The dependent claims define preferred embodiments.

According to the invention, the textile sample is illuminated with both ultraviolet (UV) and visible electromagnetic radiation. The fluorescent radiation emitted due to the UV radiation and the reflected visible radiation are both detected and combined to create a "brightness" measurement. Moreover, both the fluorescent and the reflected radiation are detected by means of an imager comprising an array of pixels. Thus, the fluorescent radiation, the reflected radiation and their combination bear embedded spatial information. In particular, the resulting brightness image turned out to be very useful for optically characterizing the textile sample.

In this document, the term "brightness" designates an intensity of both fluorescent and reflected radiation. As generally accepted, the ultraviolet range of the electromagnetic spectrum contains wavelengths between 10 nm and 400 nm, whereas the visible range contains wavelengths between 400 nm and 700 nm.

The apparatus for optically characterizing a textile sample comprises a presentation subsystem having a viewing window. A radiation subsystem has a radiation source for directing a desired first radiation in the ultraviolet range of the electromagnetic spectrum and a desired second radiation in the visible range of the electromagnetic spectrum through the viewing window toward the sample, and thereby causing the sample to produce both emission fluorescent radiation and a reflected radiation. A sensing subsystem comprises an imager for capturing the fluorescent radiation and the reflected radiation in an array of pixels, where each pixel records an intensity of both the fluorescent radiation and the reflected radiation at the pixel location. A control subsystem comprises a processor for controlling the presentation subsystem, the radiation subsystem, and the sensing subsystem, and creates a fluorescent and reflected radiation image containing both spectral information and spatial information in regard to the fluorescent radiation and the reflected radiation of the sample.

In some embodiments, the presentation subsystem further comprises a sample press for pressing the sample against the viewing window.

In some embodiments, the presentation subsystem further comprises calibration tiles for producing fluorescent radiation and reflected radiation with known characteristics in response to radiation having known characteristics.

In some embodiments, the radiation subsystem further comprises optics for shaping and/or filtering the first radiation and the second radiation from the radiation source to produce the first radiation and/or the second radiation.

In some embodiments, the radiation subsystem further comprises a detector for detecting characteristics of the first radiation and/or the second radiation.

In some embodiments, the radiation source is configured to produce the first radiation and the second radiation at a desired intensity distribution.

In some embodiments, the radiation source is configured to produce the first radiation and the second radiation in discrete radiation ranges.

In some embodiments, the radiation source is configured to produce the first radiation and the second radiation with an intensity distribution that varies in time.

In some embodiments, the radiation source is configured to produce the first radiation and the second radiation sequentially.

In some embodiments, the radiation source is configured to produce the first radiation and the second radiation simultaneously.

In some embodiments, the radiation source is configured to produce the first radiation and the second radiation in a temporally offset way, such that they partially overlap in time.

In some embodiments, the radiation source is configured to produce the first radiation and/or the second radiation periodically in time.

In some embodiments, the array of pixels is a two-dimensional array of pixels.

In some embodiments, the sensing subsystem further comprises a variable filter for selectively prohibiting portions of the fluorescent radiation and/or the reflected radiation from achieving the imager.

In some embodiments, the control subsystem further comprises a machine interface for receiving commands from and sending information to another instrument.

In some embodiments, the control subsystem further comprises a human interface for receiving commands from and sending information to a user.

In some embodiments, the control subsystem is configured to classify patterns in the fluorescent and/or reflected radiation image, including a percentage of the fluorescent and/or reflected radiation image individually represented by each one of the patterns.

In some embodiments, the control subsystem is configured to classify patterns in the fluorescent and/or reflected radiation image, including an orientation of each one of the patterns, where the orientation is at least one of horizontal, vertical, and non-ordinal.

According to another aspect of the invention, there is described a method for optically characterizing a textile sample. The method comprises the steps of: presenting the sample against a viewing window with a presentation subsystem; directing a desired first radiation in the ultraviolet range of the electromagnetic spectrum and a desired second radiation in the visible range of the electromagnetic spectrum from a radiation source through the viewing window toward the sample, thereby causing the sample to produce a fluorescent radiation and a reflected radiation; capturing the fluorescent radiation and the reflected radiation with a sensing subsystem including an imager in an array of pixels, where each pixel records an intensity of both the fluorescent radiation and the reflected radiation at the pixel location; and with a processor, controlling the presentation subsystem, the radiation subsystem, and the sensing subsystem, and creating a fluorescent and reflected radiation image containing both spectral information and spatial information in regard to the fluorescent radiation and the reflected radiation of the sample.

Some embodiments further comprise pressing the sample against the viewing window with a press.

Some embodiments further comprise shaping and/or filtering first radiation and the second radiation from the radiation source with optics before the first radiation and/or the second radiation achieves the sample.

Some embodiments further comprise detecting characteristics of the first radiation and/or the second radiation with a detector.

Some embodiments further comprise producing the first radiation and the second radiation at a desired intensity distribution.

Some embodiments further comprise producing the first radiation and the second radiation in discrete radiation ranges.

Some embodiments further comprise producing the first radiation and the second radiation with an intensity distribution that varies in time.

Some embodiments further comprise producing the first radiation and the second radiation sequentially.

Some embodiments further comprise producing the first radiation and the second radiation simultaneously.

Some embodiments further comprise producing the first radiation and the second radiation in a temporally offset way, such that they partially overlap in time.

Some embodiments further comprise producing the first radiation and/or the second radiation periodically in time.

Some embodiments further comprise selectively prohibiting the fluorescent radiation and the reflected radiation, respectively, from achieving the imager.

Some embodiments further comprise classifying patterns in the fluorescent and/or reflected radiation image, including a percentage of the fluorescent and/or reflected radiation image individually represented by each one of the patterns.

Some embodiments further comprise classifying patterns in the fluorescent and/or reflected radiation image, including an orientation of each one of the patterns, where the orientation is at least one of horizontal, vertical, and non-ordinal.

DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIGS. 2A-2E are graphs of radiation source wavelength versus output level for a selection of radiation profiles, according to various embodiments of the present invention.

FIG. 3C is a fluorescence graph of radiation level versus fluorescence level for three different fluorescence wavelengths, according to an embodiment of the present invention.

DESCRIPTION

Figure 1:
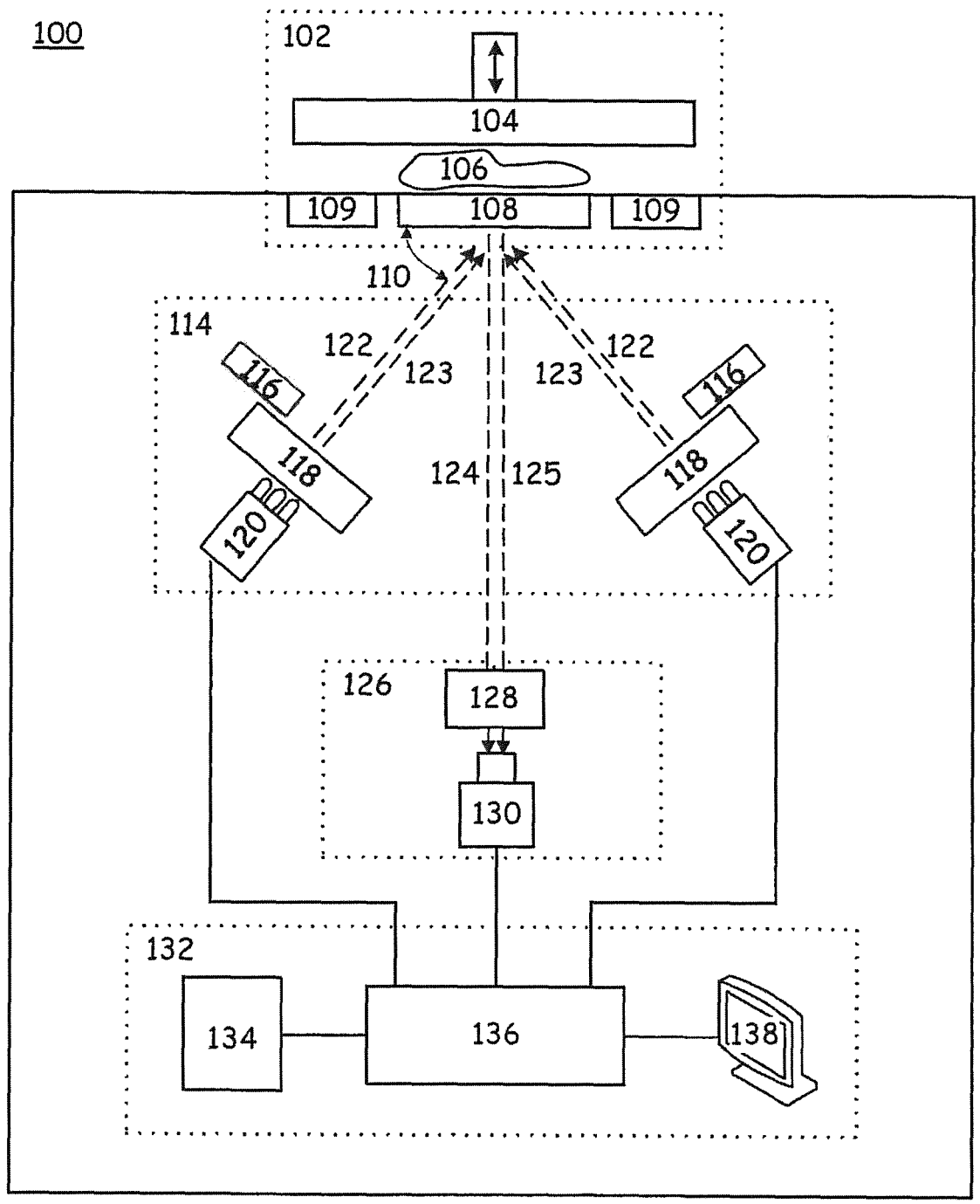
FIG. 1 is a functional block diagram of a measurement device, according to an embodiment of the present invention.

With reference now to FIG. 1, there is depicted an apparatus 100 according to the invention, which can be used for both offline and online measurements. The apparatus 100 includes a sample presentation subsystem 102, a radiation subsystem 114, a sensing subsystem 126, and a control subsystem 132, each as explained in more detail below.

FIG. 1 also shows additional aspects of the apparatus 100, which include a sample material 106 to be measured, a sample press 104, a sample or viewing window 108, reference fluorescent tiles 109, radiation sources 120, radiation shaping and filtering optics 118, radiation measurement radiometers 116, a variable optical filter 128, an imager 130, a signal processor 136, a user interface 138, and a machine interface 134, all of which are described in more detail within their relevant subsystems, below.

Sample Presentation Subsystem

The sample presentation subsystem 102 presents the sample fluorescent material 106 to the apparatus 100. The sample 106 may be any form of textile including, but not limited to, fibers, slivers, or fabrics. Some embodiments include two presentation goals. One is to present as much of the sample 106 to the apparatus 100 as reasonable, and the other is to present a consistent sample angle. One method to realize these goals is by using a sample press 104 that presses the sample 106 to the sample window 108 using a consistent pressure.

The sample presentation subsystem 102 also includes reference fluorescent tiles 109, whose reflected radiation and fluorescent characteristics are known. The intent of the reference fluorescent tiles 109 is to allow the apparatus 100 to self-calibrate to a known reference reflected radiation and fluorescence level. Furthermore, it serves as a self-test where the apparatus 100 can automatically detect malfunctioning situations due to a component failure, and so forth. When the apparatus 100 is measuring a sample 106, the reference fluorescent tiles 109 can either be shielded from radiation 122, 123 so that they do not reflect/fluoresce, or the reflection/fluorescence that they produce can be shielded from an imager 130 in some manner, so that they do not confound the fluorescence readings from the sample 106.

Radiation Subsystem

The radiation subsystem 114 is responsible for radiating and exciting the fluorescent sample 106 with radiation 122, 123 having a desired profile in terms of constituent wavelengths and their associated energies. Specifically, the intent is to control and ensure a known radiation 122, 123 profile on the sample 106. The desired radiation 122, 123 profile is dependent, at least in part, on the characteristics of sample 106 and the properties of the sample 106 to be measured. The desired radiation 122, 123 profile is controlled as described hereinafter. Some parameters of the radiation 122, 123 include, but are not limited to, wavelength, power, beam uniformity, and beam angle 110, which is the angle between radiation 122, 123 emitted by a radiation source 120 and the plane of the sample window 108. The beam angle 110 can be set, for instance, at forty-five degrees, as shown in FIG. 1.

The radiation sources 120 direct a first radiation 122 in the ultraviolet range of the electromagnetic spectrum and a second radiation 123 in the visible range of the electromagnetic spectrum through the sample window 108 toward the sample 106. The first radiation 122 and the second radiation 123 can be emitted sequentially, simultaneously or in a temporally offset way, such that they partially overlap in time. The first radiation 122 and/or the second radiation 123 can be emitted periodically in time, i.e., can be periodically be switched on and off. A sequential emission can be controlled by the processor 136. The first radiation 122 can cause the sample 106 to produce a fluorescent radiation 124. The first radiation 122 and/or the second radiation 123 can cause the sample to produce a reflected radiation 125.

The radiation subsystem 114 may include multiple radiation sources 120 arranged in different configurations. For example, in one embodiment, the configuration may incorporate two radiation sources 120 that are directed in opposite directions, as shown in FIG. 1. Whereas in another embodiment, it may incorporate four radiation sources 120, where the sample 106 is radiated from four different directions. Each of the multiple radiation sources 120 can be configured to emit both the first radiation 122 and the second radiation 123, as shown in FIG. 1. Alternatively, one of the multiple radiation sources 120 can be configured to emit only the first radiation 122, whereas another one of the multiple radiation sources 120 can be configured to emit only the second radiation 123.

In still another embodiment, the radiation subsystem 114 may include only one radiation source 120. In this case, the radiation source 120 is configured to emit both the first radiation 122 and the second radiation 123, be it sequentially or simultaneously.

In some embodiments, the radiation sources 120 can be moved within the system 100. For example, in some embodiments the sources 120 can be moved to provide different incident angles of the radiation 122 on the sample window 108. In some embodiments, the sources 120 can be moved so that they have a different proximity to the sample window 108, or a different radial angle.

An example of a radiation source 120 may include, but is not limited to, one or more of light emitting diodes (LED), halogen lamps, mercury vapor lamps, incandescent lamps, deuterium lamps, fluorescent lamps, and xenon lamps. Furthermore, each radiation source 120 may incorporate one or more of the afore-mentioned lamps. For example, one embodiment may include several groups of ultraviolet LEDs emitting the first radiation 122 and visible LEDs emitting the second radiation 123. In such an embodiment, each LED group can be controlled separately from the other groups by the processor 136.

In one embodiment, a color measurement is made on the sample 106 in the CIELAB color space, using the irradiation with the second, visible radiation 123. The color image of the sample 106 is treated in the same manner as described below for all other images.

The output levels and spectral characteristics of the radiation sources 120 can be customized for a given brightness application and measurement. FIGS. 2A-2D exemplify such a customization for the first radiation 122 only. The graphs 200a-200d depict the radiation 122 wavelength on the x-axis 204, and the radiation 122 output level on the y-axis 202. In these examples, there are two groups of ultraviolet LEDs operating at 360 nm and 380 nm, in various combinations and at various intensities.

Figure 2A:
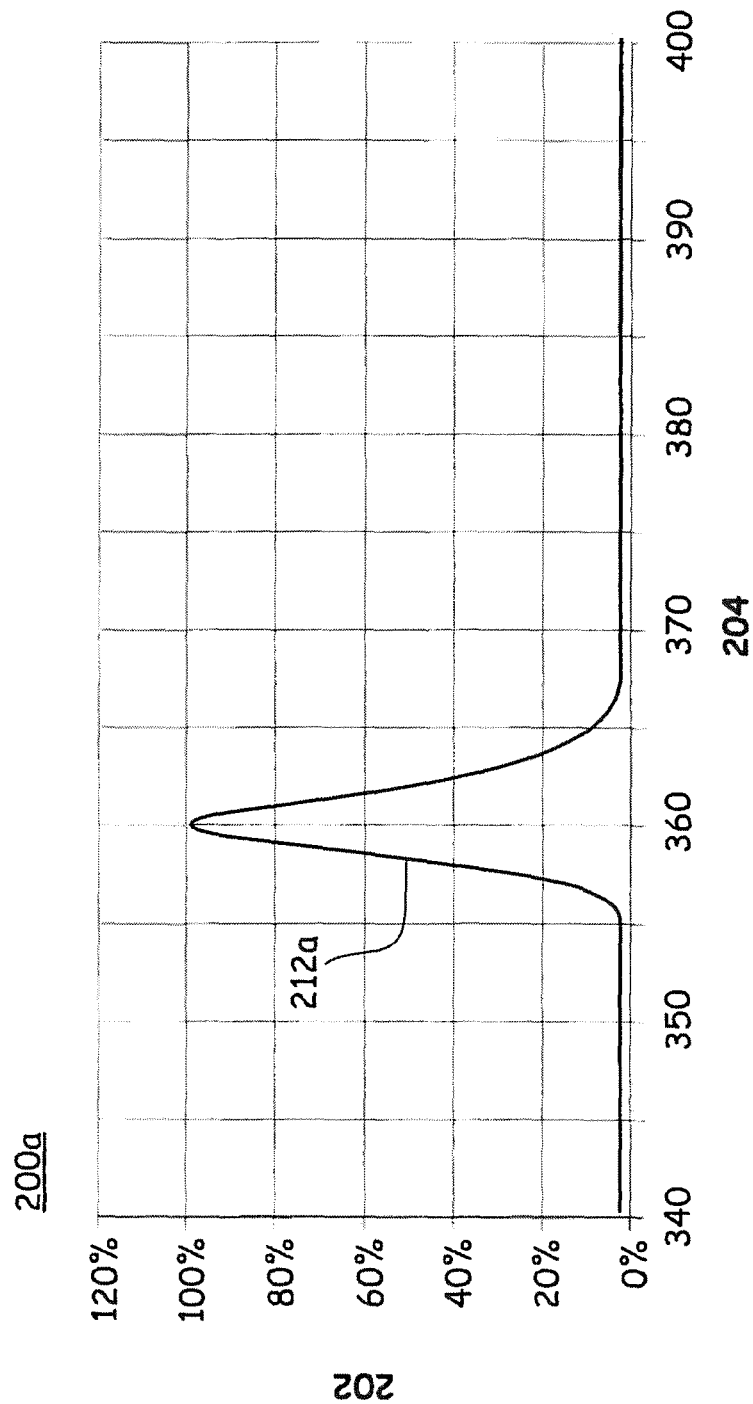
Figure 2C:
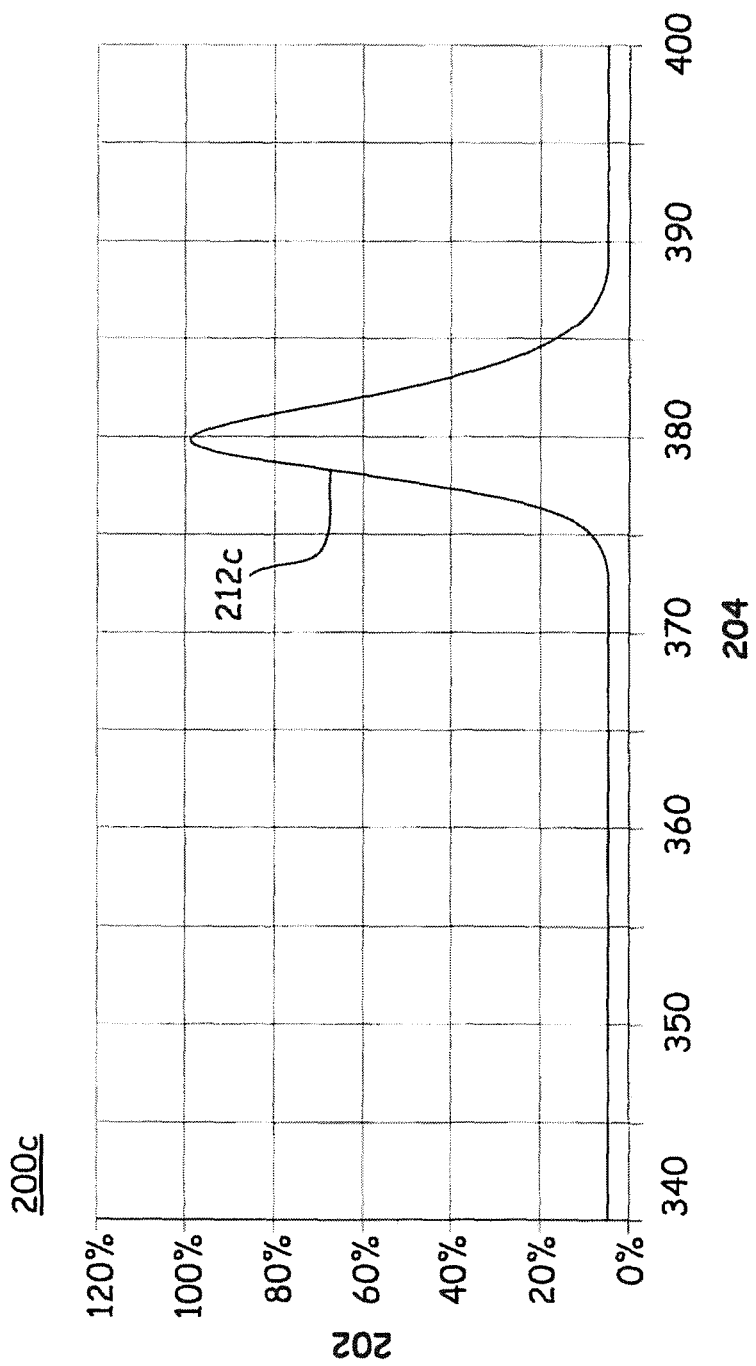
Figure 2D:
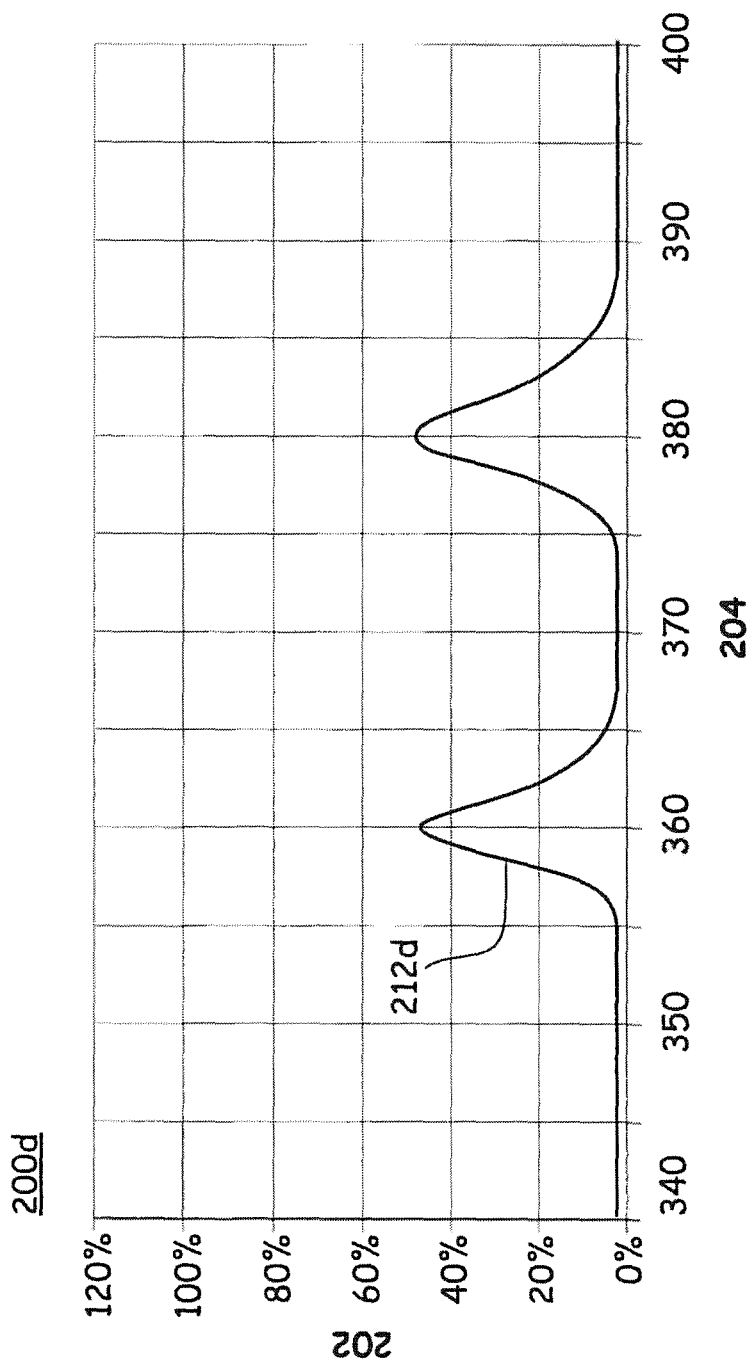

In graph 200a of FIG. 2A, the 360-nm LED group is operational at its full output level, as depicted by spectrum 212a. In graph 200b of FIG. 2B, the 360-nm LED group is operating at the 50% output level, as depicted by spectrum 212b. In both FIGS. 2A and 2B, the 380-nm LED group is completely turned off FIG. 2C depicts an example 200c where the 380-nm LED group is operating at its full output level, but the 360-nm LED group is completely turned off. FIG. 2D shows yet another example 200d where both LED groups are running at a 50% output level. Other combinations of wavelength and output level are also contemplated herein.

Figure 2E:
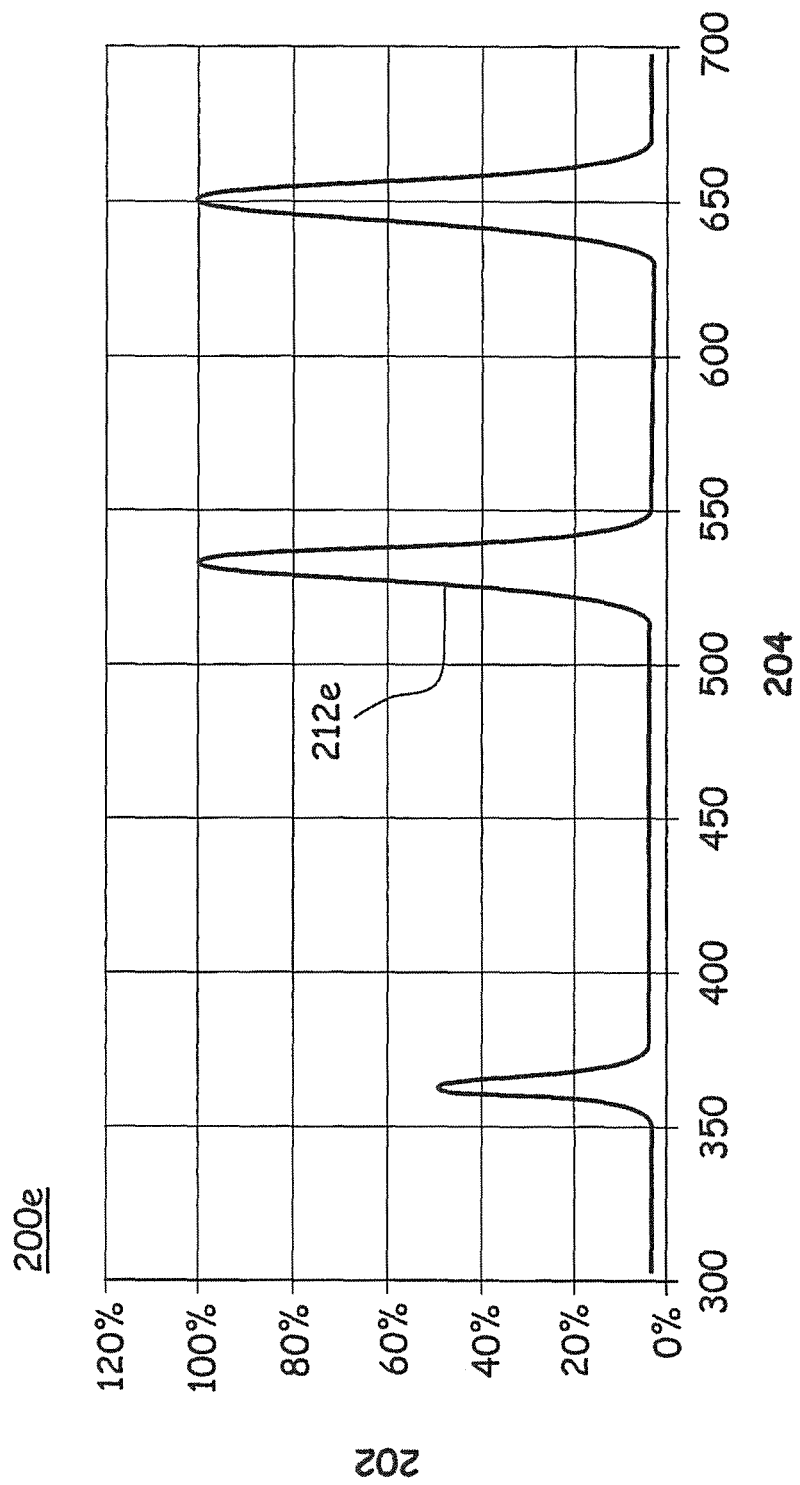

FIG. 2E shows a graph 200e with a spectrum 212e built up from both the first radiation 122 and the second radiation 123. A first peak of the spectrum 212e at 360 nm (UV) is due to the first radiation 122. A second peak at 530 nm (green) and a third peak at 650 nm (red) are due to the second radiation 123. The first radiation 122 is emitted by a first group of UV LEDs, whereas the second radiation 123 is emitted by a second group of green LEDs and a third group of red LEDs, respectively.

One design goal is to maintain radiation 122, 123 uniformity and stability over the area of the sample window 108 and/or over the area of the sample 106. One approach is to use radiation 122, 123 shaping and filtering optics 118 to fine tune the radiation 122, 123 to a desired wavelength range, and to shape the radiation 122, 123 for uniformity, directionality, and coverage. In some embodiments, the radiation 122, 123 is monitored and controlled through closed-loop feedback control via radiation 122, 123 detectors 116.

Sensing Subsystem

The sensing subsystem 126 is responsible for sensing and measuring a fluorescent radiation 124 and a reflected second radiation 125 produced by the sample 106 while it is irradiated.

One goal of the sensing subsystem 126 can be to spectrally separate a portion of the reflected radiation 125 in the same wavelength as the first radiation 122 from the emitted fluorescent signal 124. One method to accomplish this is with a variable optical filter 128. For example, in one embodiment where the sample 106 includes an optical whitener, the radiation sources 120 are set to emit the first radiation 122 in an ultraviolet spectral range of 340-400 nm, and the fluorescent emissions 124 are in a 420-470 nm spectral range. In this case, the variable optical filter 128 rejects any spectral signals in 340-400 nm range, and only passes radiation in the 420-470 nm range for capturing the fluorescent radiation 124. Alternately, for another application, the variable optical filter 128 rejects one range and passes another range, as indicated by the given application. One method to implement the variable optical filter 128 is to incorporate a filter-wheel with several band pass filters, where the processor 136 controls the filter-wheel and selects the appropriate band pass filter for a given application.

The actual sensing and measuring is performed by the imager 130. The imager 130 not only measures the amount of fluorescence emissions 124 and reflected radiation 125, but also measures the distribution and spatial characteristic of the fluorescence emissions 124 and reflected radiation 125 within the field of view of the imager 130. In one embodiment, the imager 130 may be a focal-plane two-dimensional array device that is sensitive in the desired fluorescent emissions 124 and reflected radiation 125 spectral ranges. In another embodiment, the imager 130 may be a line scan array that is scanned across the field of view to create a two-dimensional image. The scanning can be accomplished either by mechanical movement of the imager 130 or via mechanical movement of a mirror onto a stationary imager 130. In yet another embodiment, the imager 130 may be a hyper-spectral imaging device. Regardless of the specific imaging method employed, the measurement for a given sample 106 includes the levels and the spectral responses, as well as the spatial information, of both the fluorescent radiation 124 and the reflected radiation 125. For the remainder of this document, we refer to this output of the imager 130 as the brightness image.

The online sensing can be done in either a static mode or a dynamic mode. In static mode, the sample 106 is brought into the field of view of the imager 130 on the sample window 108 and stops for the measurements. In dynamic mode, the sample 106 moves across the sample window 108, and the radiation subsystem 114 and the sensing subsystem 126 operate at a speed that is fast enough related to the speed of the sample movement. In an offline mode, the sample 106 can be placed on the sample 108 manually, as desired.

Control Subsystem

The control subsystem 132 is responsible for controlling, processing, and interfacing functions of the system 100. This is accomplished under the control of a processor 136. The control functions include, but are not limited to, controlling the operation of the other subsystems in the manner as generally described elsewhere herein. It also processes the image via the measurement method selected. The result of the measurement method is communicated to the user interface 138 and/or to a machine interface 134. The machine interface 134 may include, but is not limited to, an electronic interface to a textile machine or an information system.

Measurement Method

Figure 4:
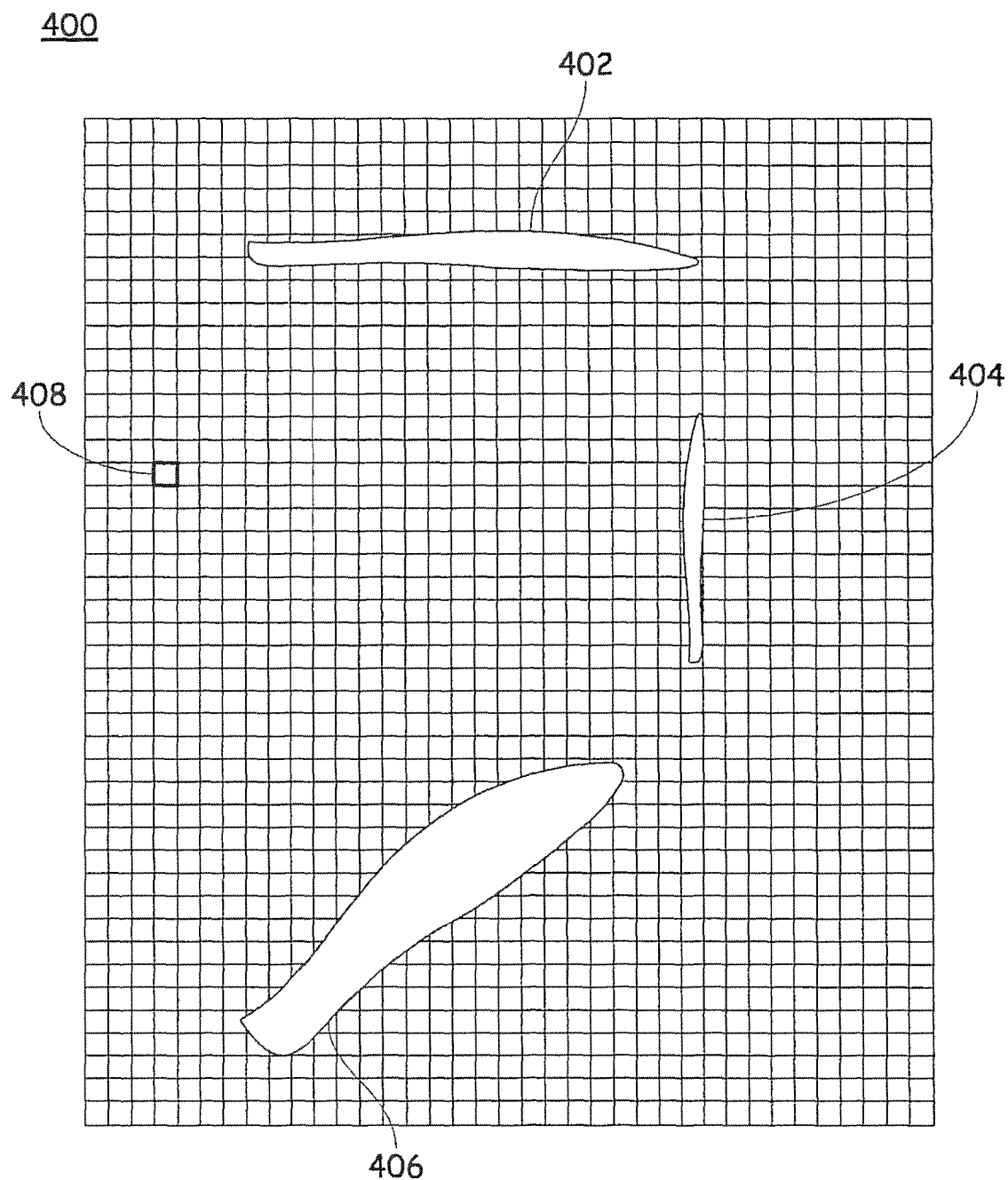
FIG. 4 is an example of a fluorescence pattern, according to an embodiment of the present invention.

The measurement method is based on processing both the fluorescent emission 124 and the reflected radiation 125 image, which may be a one- or two-dimensional image, where each pixel 408 (one image element, as depicted in FIG. 4) represents the brightness level of a particular location on the sample 106. The measurements may include, but are not limited to, two categories, which are (a) statistical analysis, and (b) pattern analysis.

Statistical Analysis

The first measurement category is based on the statistical analysis, which provides basic statistical assessment of the brightness level, which may include (a) average brightness level, (b) minimum brightness level and location of same, (c) maximum brightness level and location of same, (d) uniformity of the brightness level, and (e) a graph of the brightness.

Therefore, for a given brightness sample 106 that is irradiated with an appropriate radiation subsystem 114, the brightness image can be presented as:

$$BI(\lambda_j) = a(\lambda_j) * FI \begin{bmatrix} i_{11} & \cdots & i_{1n} \\ \vdots & i_{xy} & \vdots \\ i_{m1} & \cdots & i_{mn} \end{bmatrix} + b(\lambda_j) * LI \begin{bmatrix} i_{11} & \cdots & i_{1n} \\ \vdots & i_{xy} & \vdots \\ i_{m1} & \cdots & i_{mn} \end{bmatrix} +, \quad (1)$$

Where:
$a(\lambda_j)$ is weighting factor for the fluorescence image of wavelengths,
where $\lambda_{min} < \lambda_j < \lambda_{max}$, j=1, 2, . . . , k,
$b(\lambda_j)$ is weighting factor for the Luminance image of wavelengths,
where $\lambda min < \lambda_j < \lambda_{max}$, j=1, 2, . . . , k,
$BI(\lambda_j)$ is the brightness image of the sample 106 for one or more ranges of wavelengths, where $\lambda min < \lambda_j < \lambda_{max}$, j=1, 2, . . . , k, FI($\lambda_j$) is the fluorescence image of the sample 106 for one or more ranges of wavelengths, where $\lambda_{min} < \lambda_j < \lambda_{max}$, j=1, 2, . . . , k, LI($\lambda_j$) is the luminance image of the sample 106 for one or more ranges of wavelengths, where $\lambda min < \lambda_j < \lambda_{max}$, j=1, 2, . . . , k, n is the number of spatial points for the image in the horizontal direction, m is the number of spatial points for the image in the vertical direction, and $i_{xy}$ is the energy level of the sample at coordinate location of x and y at wavelength $\lambda_j$.

The statistical assessment of the brightness level for the sample 106 can be computed as:

$$Avg(\lambda_j) = \overline{BI(\lambda_J)} = \frac{\sum_{x=1}^{n} \sum_{y=1}^{m} i_{xy}}{m * n}, \quad (2)$$

$$Min(\lambda_j) = min(BI(\lambda_j)) = min\begin{bmatrix} i_{11} & \cdots & i_{1n} \\ \vdots & i_{xy} & \vdots \\ i_{m1} & \cdots & i_{mn} \end{bmatrix}, \quad (3)$$

$$Max(\lambda_j) = max(BI(\lambda_j)) = max\begin{bmatrix} i_{11} & \cdots & i_{1n} \\ \vdots & i_{xy} & \vdots \\ i_{m1} & \cdots & i_{mn} \end{bmatrix}, \text{ and} \quad (4)$$

$$Unif(\lambda_j) = 100 * \left(1 - \frac{std(BI(\lambda_j))}{Avg(\lambda_j)}\right), \quad (5)$$

where:

Avg($\lambda_j$) is the overall brightness level of the sample 106 for a single range or multiple ranges of wavelengths, where $\lambda min < \lambda_j < \lambda_{max}$, i=1, 2, . . . , n, Min($\lambda_j$) is the minimum brightness level of the sample 106 for a single range or multiple ranges of wavelengths, where $\lambda min < \lambda_j < \lambda_{max}$, i=1, 2, . . . , n, Max($\lambda_j$) is the maximum brightness level of the sample 106 for a single range or multiple ranges of wavelengths, where $\lambda min < \lambda_j < \lambda_{max}$, i=1, 2, . . . , n, Unif($\lambda_j$) is the uniformity of the brightness level of the sample 106 for a single range or multiple ranges of wavelengths where $\lambda_{min} < \lambda_j < \lambda_{max}$, i=1, 2, . . . , n, n is the number of spatial points for the image in horizontal direction, m is the number of spatial points for the image in vertical direction, and $i_{xy}$ is the combined incident radiation and fluorescence emissions level of the sample 106 at coordinate location of x and y at wavelength $\lambda_j$.

We also define the term "fluorescence graph", which presents the emitted fluorescence level of the sample 106 to different first-radiation 122 parameters. The intent of the fluorescent graph is to enable an easier and better characterization of the fluorescence of the sample 106. This also may be beneficial during the formulation of the fluorescent pigments process.

As stated earlier, the radiation subsystem 114 can be controlled by processor 136 for different radiation 122, 123 levels and spectral characteristics. Furthermore, the sensing subsystem 126 can also be controlled by processor 136 for spectral sensing of the emitted signals 124, 125.

Figure 3A:
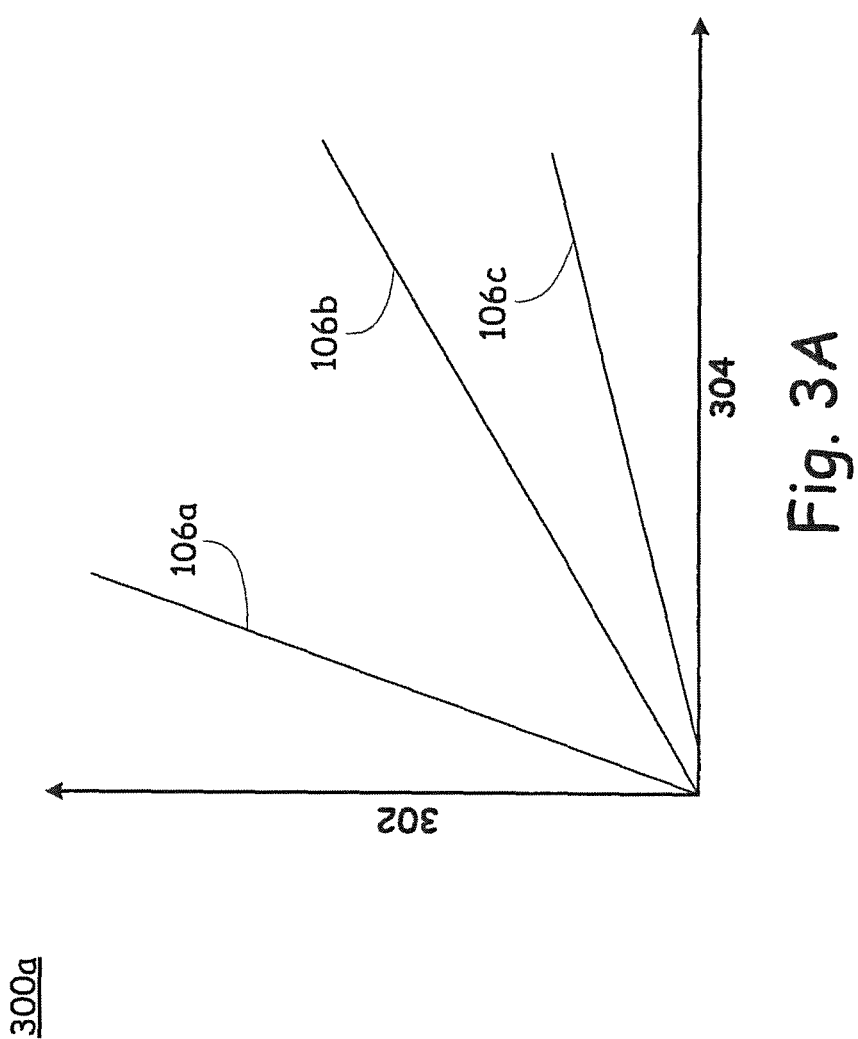
FIG. 3A is a fluorescence graph of radiation level versus fluorescence level for three different materials, according to an embodiment of the present invention.
Figure 3B:
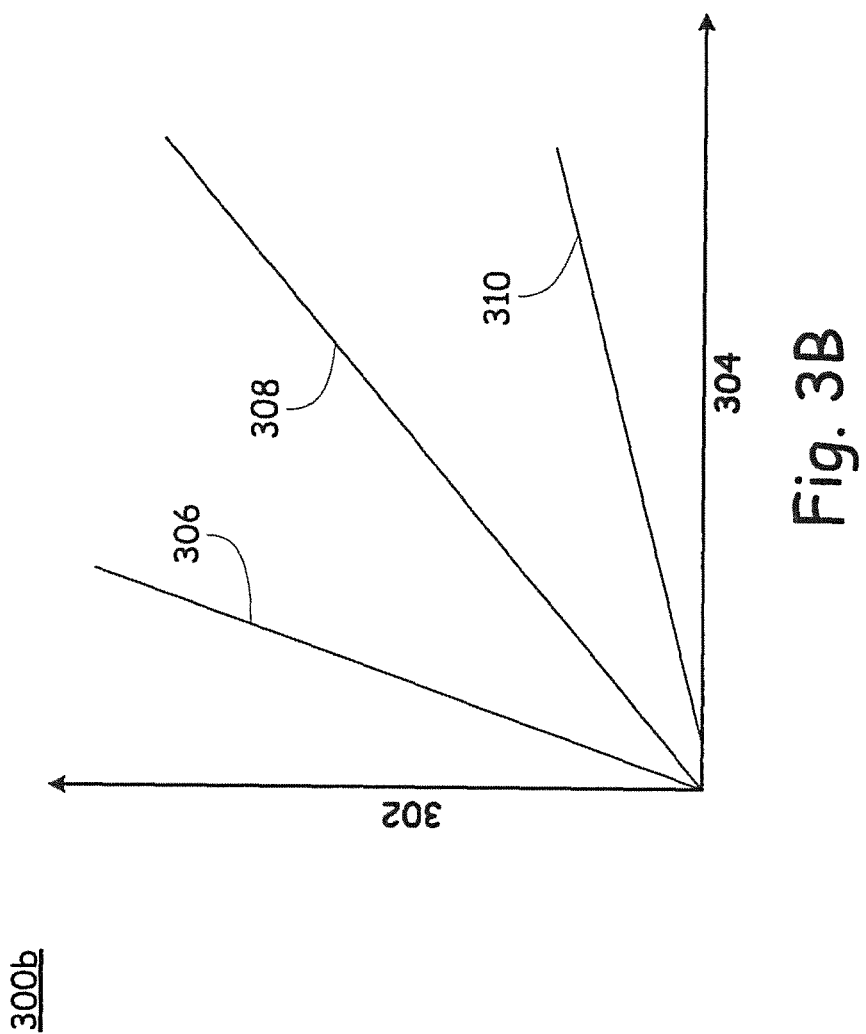
FIG. 3B is a fluorescence graph of radiation level versus fluorescence level for three different radiation wavelengths, according to an embodiment of the present invention.

FIGS. 3A-3C depict an example of how various samples 106a-106c react to various first-radiation 122 levels. This characterization quantifies the optimum first-radiation 122 level for a given fluorescent application requirement.

FIG. 3A depicts an example 300a where three different samples 106a-106c of fluorescent pigments are exposed to varying levels of first radiation 122, and graphed as the fluorescence level of each sample 106a-106c on the y-axis 302, versus the first-radiation 122 level on the x-axis 304. This enables quantitative comparison and selection of the optimum samples 106 of fluorescent pigments for a given application.

FIG. 3B shows an example 300b where one sample 106 of a fluorescent pigment is exposed to three different first radiations 122 with different spectral characteristics. This results in graphs 306, 308, and 310. FIG. 3C shows an example 300c where one sample 106 of a fluorescent pigment is exposed to one first radiation 122 with different spectral characteristics, and produces fluorescence at three wavelengths 312, 314, and 316. Based on the application, these graphs can help with understanding and selecting an optimum radiation source and emission outputs.

Pattern Analysis

The second measurement category is based on pattern analysis, which provides pattern information once it is found. The main difference between statistical analysis and pattern analysis is the inclusion of spatial information. In pattern analysis, the location and relationship among all pixels in an image are considered, whereas in statistical analysis, the spatial information is not considered. The pattern analysis can be performed with the fluorescent image, with the reflected image and/or with the brightness image. For the sake of simplicity, the following description refers to the brightness image only, without loss of generality.

Pattern analysis may include (a) the number of patterns found in the brightness image, (b) the total area of all patterns in the brightness image, (c) the average size of all patterns, (d) the percentage of patterns with a horizontal orientation, (e) the percentage of patterns with a vertical orientation, and (f) the percentage of patterns with a non-ordinal, or random, orientation.

We define the pattern set:

$$P(\lambda_j) = \{p_1, p_2, \ldots, p_l\}, \quad (6)$$

where P($\lambda_j$) is a set of fluorescent patterns $p_1$ through $p_l$ that are present in the brightness image FI($\lambda_j$) for a single range or multiple ranges of wavelengths where $\lambda min < \lambda_j < \lambda_{max}$, j=1, 2, . . . , k.

Each pattern $p_l$ contains a group of pixels $i_{xy}$ in a cluster with a clustering requirement. Clustering requirements can vary from application to application. One example is when all adjacent $i_y$ having values larger than either a static or dynamically computed threshold.

Examples of fluorescent patterns 402, 404, and 406 are shown in pattern diagram 400 of FIG. 4. In this example, there are three fluorescent patterns 402, 404, and 406, where each pattern 402, 404, and 406 has a different orientation and size as shown. For example, pattern 402 is a substantially horizontal pattern, while pattern 404 is a substantially vertical pattern. Pattern 406 is a non-ordinal or random pattern.

In addition to categorizing the orientation of the patterns 402, 404, and 406, the size of each pattern 402, 404, and 406 is also computed. In the example 400 as depicted, pattern 402 is approximately 5.2% of the total field of view, pattern 404 is approximately 2.1% of the total field of view, and pattern 406 is approximately 11.2% of the total field of view.

Thus, various embodiments of the apparatus and method as described herein provide a more thorough analysis of the fluorescence of textiles, by providing fluorescence data at highly selectable radiation 122 profiles, and providing fluorescence data in a two-dimensional image of the sample 106, along with other benefits as described herein.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An apparatus (100) for optically characterizing a textile sample (106), the apparatus (100) comprising:
  a presentation subsystem (102) comprising a viewing window (108),
  a radiation subsystem (114) comprising a radiation source (120) for directing a desired first radiation (122) in the ultraviolet range of the electromagnetic spectrum and a desired second radiation (123) in the visible range of the electromagnetic spectrum through the viewing window (108) toward the sample (106), and causing the sample (106) to produce a fluorescent radiation (124) and a reflected radiation (125),
  a sensing subsystem (126) comprising an imager (130) for capturing the fluorescent radiation (124) and the reflected radiation (125) in an array of pixels (408), where each pixel (408) records an intensity of both the fluorescent radiation (124) and the reflected radiation (125) at the pixel location, and
  a control subsystem (132) comprising a processor (136) for controlling the presentation subsystem (102), the radiation subsystem (114), and the sensing subsystem (126), and for creating a fluorescent and reflected radiation image (400) containing both spectral information and spatial information in regard to the fluorescent radiation (124) and the reflected radiation (125) of the sample (106),
  wherein the control system (132) is configured to perform a pattern analysis with the fluorescent and reflected radiation image (400), which pattern analysis includes at least one of,
    (a) a number of patterns found in the fluorescent and reflected radiation image (400),
    (b) a total area of all patterns in the fluorescent and reflected radiation image (400),
    (c) an average size of all patterns in the fluorescent and reflected radiation image (400),
    (d) a percentage of patterns with a horizontal orientation in the fluorescent and reflected radiation image (400),
    (e) a percentage of patterns with a vertical orientation in the fluorescent and reflected radiation image (400), and
    (f) a percentage of patterns with a nonordinal, or random, orientation in the fluorescent and reflected radiation image (400).

2. The apparatus of claim 1, wherein the presentation subsystem (102) further comprises a sample press (104) for pressing the sample (106) against the viewing window (108).

3. The apparatus of claim 1, wherein the presentation subsystem (102) further comprises calibration tiles (109) for producing fluorescent radiation (124) and reflected radiation (125) with known characteristics in response to radiation (122) having known characteristics.

4. The apparatus of claim 1, wherein the radiation subsystem (114) further comprises optics (118) for at least one of shaping or filtering the first radiation (122) and the second radiation (123) from the radiation source (120) to produce at least one of the first radiation (122) or the second radiation (123).

5. The apparatus of claim 1, wherein the radiation subsystem (114) further comprises a detector (116) for detecting characteristics of at least one of the first radiation (122) or the second radiation (123).

6. The apparatus of claim 1, wherein the radiation source (120) is configured to produce the first radiation (122) and the second radiation (123) with an intensity distribution that varies in time.

7. The apparatus of claim 1, wherein the radiation source (120) is configured to produce the first radiation (122) and the second radiation (123) sequentially.

8. The apparatus of claim 1, wherein the radiation source (120) is configured to produce the first radiation (122) and the second radiation (123) simultaneously.

9. The apparatus of claim 1, wherein the radiation source (120) is configured to produce the first radiation (122) and the second radiation (123) in a temporally offset way, such that they partially overlap in time.

10. The apparatus of claim 1, wherein the radiation source (120) is configured to produce at least one of the first radiation (122) or the second radiation (123) periodically in time.

11. The apparatus of claim 1, wherein the array of pixels (408) is a two-dimensional array of pixels (408).

12. The apparatus of claim 1, wherein the sensing subsystem (126) further comprises a variable filter (128) for selectively prohibiting portions of at least one of the fluorescent radiation (124) or the reflected radiation (125) from achieving the imager (130).

13. The apparatus of claim 1, wherein the control subsystem (132) is configured to classify patterns (402, 404, 406) in at least one of the fluorescent or reflected radiation image (400), including a percentage of at least one of the fluorescent or reflected radiation image (400) individually represented by each one of the patterns (402, 404, 406).

14. The apparatus of claim 1, wherein the control subsystem (132) is configured to classify patterns (402, 404, 406) in at least one of the fluorescent or reflected radiation image (400), including an orientation of each one of the patterns (402, 404, 406), where the orientation is at least one of horizontal, vertical, and non-ordinal.

15. A method for optically characterizing a textile sample (106),
  the method comprising the steps of:
    presenting the sample (106) against a viewing window (108) with a presentation subsystem (102),
    directing a desired first radiation (122) in the ultraviolet range of the electromagnetic spectrum and a desired second radiation (122) in the visible range of the electromagnetic spectrum from a radiation source (120) through the viewing window (108) toward the sample (106), thereby causing the sample (106) to produce a fluorescent radiation (124) and a reflected radiation (125),
    capturing the fluorescent radiation (124) and the reflected radiation (125) with a sensing subsystem (126) including an imager (130) in an array of pixels (408), where each pixel (408) records an intensity of both the fluorescent radiation (124) and the reflected radiation (125) at the pixel location, with a processor (136), controlling the presentation subsystem (102), the radiation subsystem (114), and the sensing subsystem (126), and creating a fluorescent and reflected radiation image (400) containing both spectral information and spatial information in regard to the fluorescent radiation (124) and the reflected radiation (125) of the sample (106), and with the processor (136), preforming a pattern analysis with the fluorescent and reflected radiation image (400), which pattern analysis includes at least one of,
   (a) a number of patterns found in the fluorescent and reflected radiation image (400),
   (b) a total area of all patterns in the fluorescent and reflected radiation image (400),
   (c) an average size of all patterns in the fluorescent and reflected radiation image (400),
   (d) a percentage of patterns with a horizontal orientation in the fluorescent and reflected radiation image (400),
   (e) a percentage of patterns with a vertical orientation in the fluorescent and reflected radiation image (400), and
   (f) a percentage of patterns with a non-ordinal, or random, orientation in the flouorescent and reflected radiation image (400).

16. The method of claim 15, further comprising pressing the sample (106) against the viewing window (108) with a press (104).

17. The method of claim 15, further comprising at least one of shaping or filtering first radiation (122) and the second radiation (123) from the radiation source (120) with optics (118) before at least one of the first radiation (122) or the second radiation achieves the sample (106).

18. The method of claim 15, further comprising detecting characteristics of at least one of the first radiation (122) or the second radiation (123) with a detector (116).

19. The method of claim 15, further comprising producing the first radiation (122) and the second radiation (123) with an intensity distribution that varies in time.

20. The method of claim 15, further comprising producing the first radiation (122) and the second radiation (123) sequentially.

21. The method of claim 15, further comprising producing the first radiation (122) and the second radiation (123) simultaneously.

22. The method of claim 15, further comprising producing the first radiation (122) and the second radiation (123) in a temporally offset way, such that they partially overlap in time.

23. The method of claim 15, further comprising producing at least one of the first radiation (122) or the second radiation (123) periodically in time.

24. The method of claim 15, further comprising selectively prohibiting the fluorescent radiation (124) and the reflected radiation (125), respectively, from achieving the imager (130).

25. The method of claim 15, further comprising classifying patterns (402, 404, 406) in at least one of the fluorescent or reflected radiation image (400), including a percentage of at least one of the fluorescent or reflected radiation image (400) individually represented by each one of the patterns (402, 404, 406).

26. The method of claim 15, further comprising classifying patterns (402, 404, 406) in at least one of the fluorescent or reflected radiation image (400), including an orientation of each one of the patterns (402, 404, 406), where the orientation is at least one of horizontal, vertical, and non-ordinal.

* * * * *